(12) United States Patent
Levy

(10) Patent No.: US 7,231,014 B2
(45) Date of Patent: Jun. 12, 2007

(54) MULTIPLE MODE FLAT PANEL X-RAY IMAGING SYSTEM

(75) Inventor: Richard M. Levy, Portola Valley, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/057,442

(22) Filed: Feb. 14, 2005

(65) Prior Publication Data

US 2006/0182219 A1    Aug. 17, 2006

(51) Int. Cl.
*G01N 23/04*    (2006.01)
*H05G 1/64*    (2006.01)

(52) U.S. Cl. .................................. 378/62; 378/98.8
(58) Field of Classification Search .................. 378/4, 378/15, 19, 42, 98.9, 62; 382/128, 132
See application file for complete search history.

(56) References Cited

U.S. PATENT DOCUMENTS

| | | | |
|---|---|---|---|
| 6,233,308 B1 * | 5/2001 | Hsieh | 378/62 |
| 6,480,732 B1 * | 11/2002 | Tanaka et al. | 600/425 |
| 6,486,808 B1 | 11/2002 | Seppi | |
| 6,510,195 B1 * | 1/2003 | Chappo et al. | 378/19 |
| 2003/0197800 A1 * | 10/2003 | Petrick et al. | 348/308 |
| 2003/0223539 A1 * | 12/2003 | Granfors et al. | 378/98.8 |
| 2004/0202281 A1 | 10/2004 | Colbeth | |
| 2005/0083120 A1 | 4/2005 | Roos et al. | |

OTHER PUBLICATIONS

International Search Report and The Written Opinion of the International Searching Authority, International Application No. PCT/US06/03798, International filing date Feb. 3, 2006, Date of mailing May 24, 2006.
U.S. Appl. No. 10/644,206, filed Aug. 20, 2003, Inventor: Dan Hardesty.
U.S. Appl. No. 10/907,747, filed Apr. 14, 2005, Inventor: Dan Hardesty.

* cited by examiner

*Primary Examiner*—Edward J. Glick
*Assistant Examiner*—Irakli Kiknadze
(74) *Attorney, Agent, or Firm*—Vedder, Price, Kaufman & Kammholz, P.C.

(57) ABSTRACT

A flat panel X-ray imaging system capable of acquiring images at multiple frame rates with multiple fields of view.

17 Claims, 2 Drawing Sheets

MULTIPLE MODE FLAT PANEL X-RAY IMAGING SYSTEM

BACKGROUND OF THE INVENTION

1. Field of the Invention

The present invention relates to X-ray radiation imaging systems, and in particular, to flat panel X-ray radiation imaging systems using solid state flat detector panels and capable of operating in multiple detection modes.

2. Description of the Related Art

The use of X-ray radiation has become a valuable and widespread tool in medical diagnoses and treatments. In film radiography, a burst of X-rays, after passing through the body, is recorded on high resolution X-ray film. In fluoroscopy, an image intensifier tube converts X-ray radiation to a video signal for viewing and recording interior body activity as a video image.

Film radiography is commonly used due to its good spatial resolution, high signal-to-noise ratio (SNR), large detection area and low cost. However, developing exposed X-ray film typically takes a minimum of ninety seconds which can be too long in emergency situations. Further, the relatively low dynamic range of X-ray film can result in under- or over-exposed images and, therefore, necessitate additional exposures which increase the aforementioned time delay as well as the X-ray dosage received by the patient.

The image intensifier tube used in fluoroscopy has a greater exposure latitude than X-ray film, but also has a more limited active detection area and lower spatial resolution. The lower spatial resolution associated with the total active area is somewhat mitigated in that the image intensifier tubes allow magnification of the central image portion, thereby providing a means to enhance visual details. However, the image intensifier tube is typically heavy, bulky and expensive, and can introduce image distortion which can only be partially removed during post processing.

A number of alternative X-ray imaging technologies have been developed. For example, one alternative, known as computed radiography, involves the use of a photostimulable phosphor plate which has the same physical appearance as a standard X-ray film cassette and provides good spatial resolution, SNR and dynamic range. However, after exposure to X-rays, the photostimulable phosphor plate must be scanned with a laser system which is large and expensive, and the readout process is just as slow as the development of film.

Another alternative which provides good spatial resolution and dynamic range, as well as the added advantage of compatibility with real time digital image processing techniques, involves the use of solid state detector panels. One such panel uses an amorphous silicon (a-Si) detector array arranged as a two dimensional matrix of pixels, each of which consists of a photosensitive element and a transistor switch. As with X-ray film cassettes, the detector array is covered with a scintillation layer to convert impinging X-rays into visible light for the photosensitive elements. Another such panel is a photoconductor panel which has a detector array of a material, e.g., amorphous selenium (a-Se), that converts impinging X-rays into electrical charges directly.

Such solid state detector panels, also referred to as flat panels, have become increasingly effective, in terms of both imaging performance and costs. Accordingly, given the increased efficiencies of such flat panel detectors, it would be desirable to be able to use such detectors for performing multiple types of X-ray imaging.

SUMMARY OF THE INVENTION

In accordance with some aspects of the presently claimed invention, a flat panel X-ray imaging system is provided which is capable of acquiring images at multiple frame rates with multiple fields of view.

In accordance with one embodiment of the presently claimed invention, a flat panel X-ray imaging system adapted to acquire images at a plurality of frame rates and with a plurality of fields of view includes an X-ray emission system, an X-ray detection system and a control system. The X-ray emission system is responsive to at least one emission control signal by providing a plurality of X-ray radiation emissions. The X-ray detection system, including a substantially planar X-ray receptor, is responsive to at least one detection control signal and respective portions of the plurality of X-ray radiation emissions following exposure thereto of a subject disposed at least partially between the X-ray emission system and the X-ray receptor by providing a plurality of image signals having a plurality of frame rates and corresponding to a plurality of images of the subject with a first portion of the plurality of subject images having a larger field of view (FOV) at a lower one of the plurality of frame rates and a second portion of the plurality of subject images having a smaller FOV at a higher one of the plurality of frame rates. The control system is coupled to the X-ray emission and detection systems, and responsive to at least a portion of a plurality of user inputs by providing the at least one emission control signal and the at least one detection control signal.

In accordance with another embodiment of the presently claimed invention, a flat panel X-ray imaging system adapted to acquire images at a plurality of frame rates and with a plurality of fields of view includes X-ray emitter means, X-ray detector means and controller means. The X-ray emitter means is for responding to at least one emission control signal by providing a plurality of X-ray radiation emissions. The X-ray detector means, including substantially planar X-ray receptor means, is for responding to at least one detection control signal and respective portions of the plurality of X-ray radiation emissions following exposure thereto of a subject disposed at least partially between the X-ray emission system and the X-ray receptor by providing a plurality of image signals having a plurality of frame rates and corresponding to a plurality of images of the subject with a first portion of the plurality of subject images having a larger field of view (FOV) at a lower one of the plurality of frame rates and a second portion of the plurality of subject images having a smaller FOV at a higher one of the plurality of frame rates. The controller means is for responding to at least a portion of a plurality of user inputs by providing the at least one emission control signal and the at least one detection control signal.

In accordance with still another embodiment of the presently claimed invention, a method for using a flat panel X-ray imaging system to acquire images at a plurality of frame rates and with a plurality of fields of view includes:

disposing a subject at least partially between an X-ray radiation source and a substantially planar X-ray receptor; and providing a plurality of X-ray radiation emissions with the X-ray radiation source in response to reception of at least one emission control signal;

providing, with the X-ray receptor, a plurality of image signals in response to reception of at least one detection control signal and respective portions of the plurality of X-ray radiation emissions following exposure thereto of the subject, wherein the plurality of image signals has a plurality of frame rates and corresponds to a plurality of images of the subject with a first portion of the plurality of subject images having a larger field of view (FOV) at a lower one of the plurality of frame rates and a second portion of the plurality of subject images having a smaller FOV at a higher one of the plurality of frame rates.

DETAILED DESCRIPTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Throughout the present disclosure, absent a clear indication to the contrary from the context, it will be understood that individual circuit elements as described may be singular or plural in number. For example, the terms "circuit" and "circuitry" may include either a single component or a plurality of components, which are either active and/or passive and are connected or otherwise coupled together (e.g., as one or more integrated circuit chips) to provide the described function. Additionally, the term "signal" may refer to one or more currents, one or more voltages, or a data signal. Within the drawings, like or related elements will have like or related alpha, numeric or alphanumeric designators. Further, while the present invention has been discussed in the context of implementations using discrete electronic circuitry (preferably in the form of one or more integrated circuit chips), the functions of any part of such circuitry may alternatively be implemented using one or more appropriately programmed processors, depending upon the signal frequencies or data rates to be processed.

Figure 1:
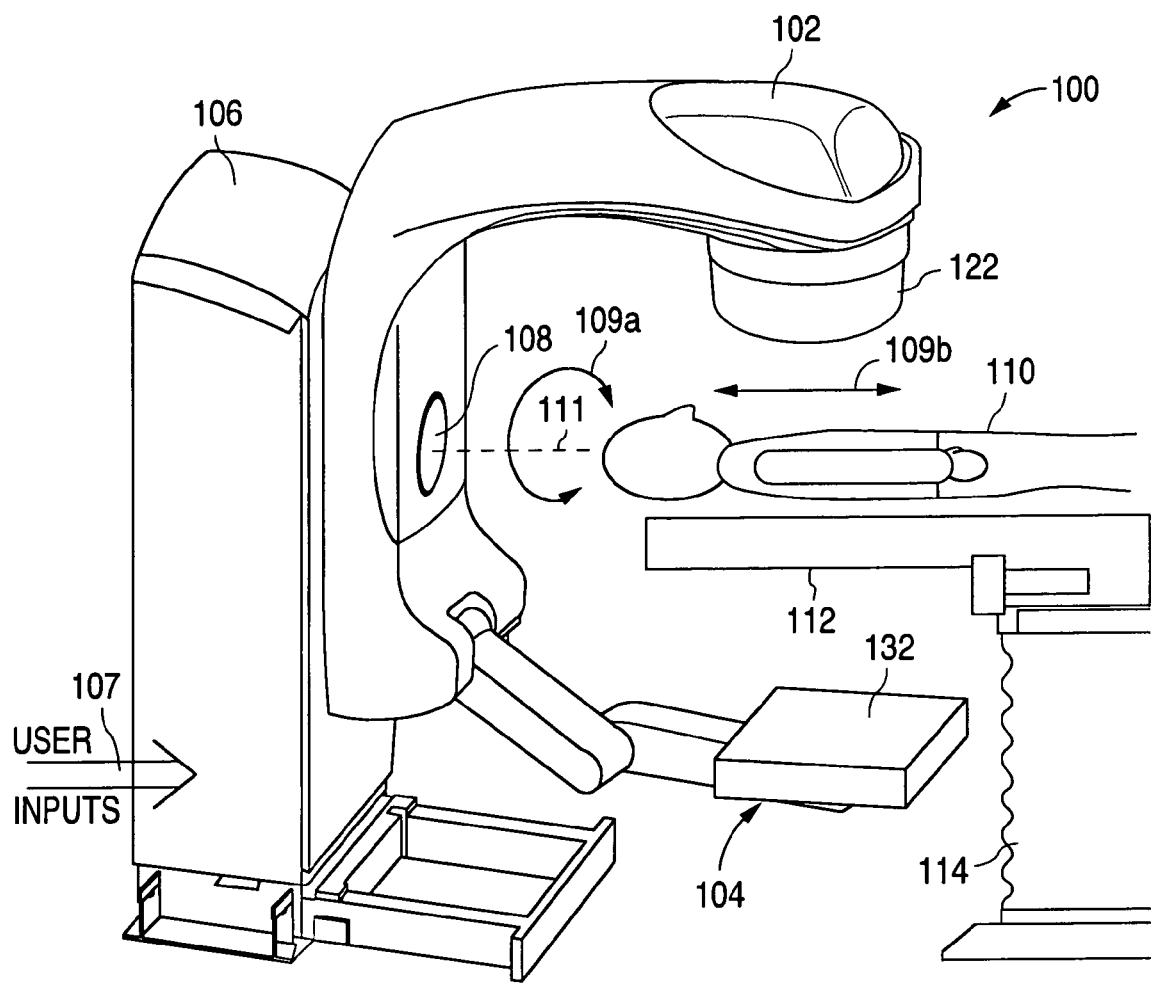
FIG. 1 depicts one example embodiment of a multiple mode flat panel X-ray imaging system in accordance with one embodiment of the presently claimed invention.

Referring to FIG. 1, a multiple mode flat panel X-ray imaging system 100 in accordance with one embodiment of the presently claimed invention includes an X-ray emission system 102, an X-ray detection system 104 and a control system 106, generally as shown. The control system 106, in conformance with a plurality of user inputs 107, controls the doses and emission patterns of the X-ray radiation emitted by the emission system 102, and the generating and processing of image signals by the detection system 104 which includes a substantially planar X-ray receptor. For obtaining two-dimensional X-ray images at different angles, as well as obtain three-dimensional images left (e.g., for computed tomography), the control system 106 can cause the emission system 102 and detection system 104, which are in substantially diametric opposition to one another, to rotate, e.g., on a pivot 108, along an arc 109 about an axis 111. The subject 110 for which the X-ray images are being obtained is substantially coaxial with the axis 111 of rotation, is supported on a platform 112 the elevation of which can be adjusted by a suitable mechanism 114, and can be moved longitudinally along a line 109b parallel with the axis 111 of rotation, as well as laterally, i.e., in a horizontal direction perpendicular to the axis 111 of rotation. Accordingly, with such a full range of linear motion and positioning (vertically, longitudinally and laterally) for the subject 110, in conjunction with the rotation of the emission 102 and detection 104 systems, virtually any form of image can be obtained, e.g., projection, fluoroscopic, radiographic, cone beam computed tomographic (CT).

It will be readily appreciated that while the mechanism of FIG. 1 is shown as being of substantially unitary construction, with the emission 102 and detection 104 systems mutually mechanically coupled, it is also within the scope of the presently claimed invention to have a system in which the emission 102 and detection 104 systems do not share a mechanical connection, but are nonetheless controlled by the control system 106 to rotate about the axis 111 in mutually diametric opposition.

Figure 2:
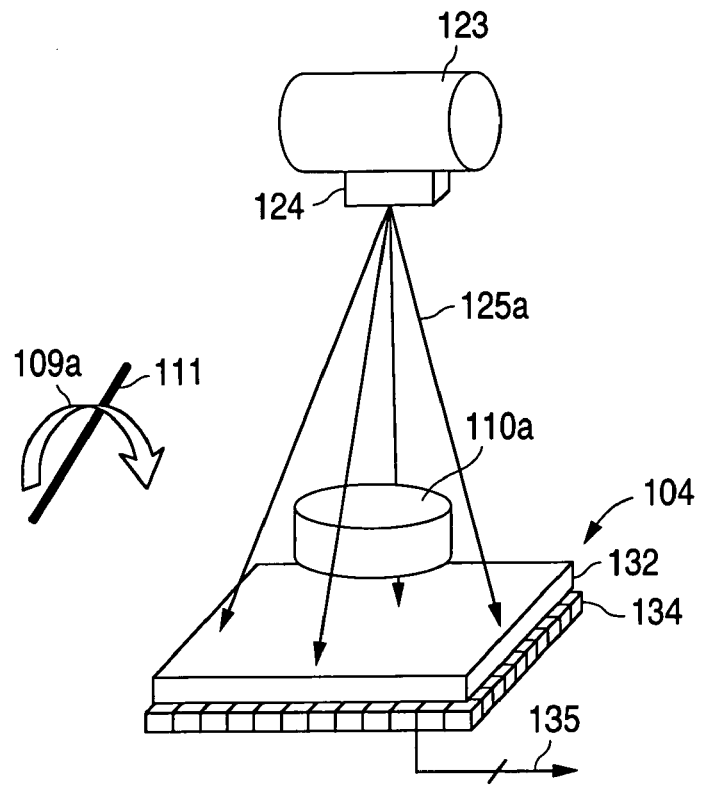
FIG. 2 depicts a volumetric scan using an X-ray imaging system such as that depicted in FIG. 1.

Referring to FIG. 2, the head 122 of the emission system 102 includes an X-ray radiation source 123 with a collimator 124 with which the emission pattern, i.e., the size and shape of the X-ray beam 125a, can be controlled. In this example, the emission pattern 125a is in the form of a cone to which a portion 110a of the subject 110 is exposed, following which the variously attenuated X-rays are absorbed by the receptor 132 of the detection system 104. The resulting pixel data signals are accessed by the receiver, or readout, circuitry 134 and processed in a conventional manner to provide image signals 135 to the control system 106. (Such a detection system operates in a conventional manner, and a more detailed discussion can be found in U.S. Pat. No. 5,970,115, the disclosure of which is incorporated herein by reference.)

Figure 3:
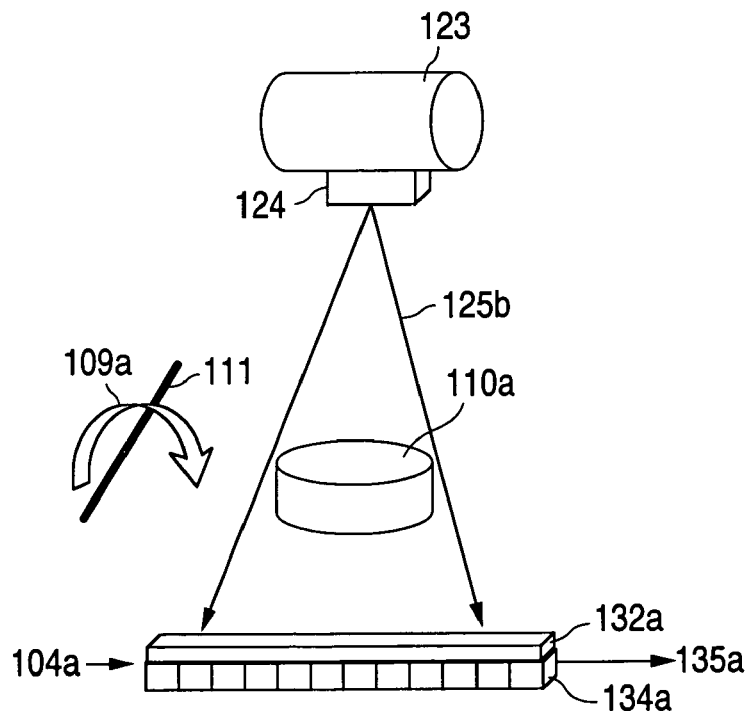
FIG. 3 depicts a cross section scan using an X-ray imaging system such as that depicted in FIG. 1.

Referring to FIG. 3, the collimator 124 can also be controlled to produce an X-ray beam in the form of a fan, or slice, 125b which, following exposure of the portion 110a of the subject 110, is absorbed by a portion 132a of the receptor 132 (e.g., one or more of a few rows or columns of pixels), following which a portion 134a of the receiver circuitry produces one (serial) or more (parallel) image signals 135a to the control system 106.

Figure 4:
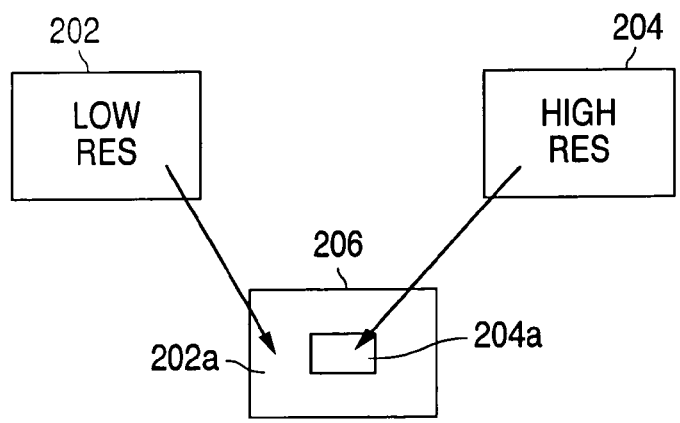
FIG. 4 depicts how the X-ray imaging system of FIG. 1 can be used to produce two images which are then combined, at least in part, to produce a composite image.

Referring to FIG. 4, in accordance with another embodiment of the presently claimed invention, the imaging system 100 can be operated in such a manner as to produce image signals corresponding to two images of varying resolutions. For example, one set of image signals can be generated during one scan (e.g., linear or rotational) corresponding to a lower resolution image 202. This can be followed by another scan for which image signals are generated corresponding to a higher resolution image 204. Additional scans producing additional images at varying resolutions can also be performed, as desired. Once these image signals have been generated, they can be combined to produce a set of image signals corresponding to a composite image 206 in which a portion, e.g., the background 202a, of the image 206 contains the lower resolution image data, while the region of interest 204a contains the higher resolution image data. This will allow an exploratory, or "scout", image (e.g., via fluoroscopic, radiographic or cone beam CT) to be taken over a large field of view at a lower image frame rate where motion artifacts (e.g., due to motion by the subject 110 during the longer time necessary for a larger area scan) are not critical. Additionally, as needed, the spatial resolution of the scan can be controlled, e.g., via pixel binning, to accommodate the desired field of view at the selected image frame rate.

Meanwhile, in the region of interest which is smaller, a higher speed scan also via fluoroscopic, radiographic or cone beam CT techniques (e.g., reading out the pixel data of interest at a higher frame rate) can be performed, thereby increasing the temporal resolution and minimizing subject motion artifacts. Additionally, as desired, the spatial resolution of the scan in the region of interest can be altered, e.g., more or less pixel binning for decreased or increased spatial resolution, respectively. As noted, additional higher resolution (temporal or spatial) images can be obtained using faster scans of the subject in regions of interest elsewhere within the overall composite image 206 area.

As should be readily appreciated, the composite image 206 can be in form of a projection view of this subject 110 in which two-dimensional image information is presented. Alternatively, the composite image 206 can be the result of a CT scan and represent three-dimensional image information in the form of a cross section view of a portion of the subject 110 (e.g., with the scans being performed circularly about the subject or helically along the subject to obtain the required image information for reconstruction as a volumetric image). As noted above, the scans can be rotational, with an initial scan corresponding to a larger field of view at a lower image frame rate to obtain an exploratory image, followed by another scan corresponding to a smaller field of view (e.g., a region of interest) at a higher image frame rate to obtain an image with increased resolution (e.g., temporal). As used in this context, field of view refers to the amount of image information used (e.g., read out or otherwise extracted from the receptor 132 of the detection system 104). For example, for a smaller field of view, pixel data from a smaller area of the receptor is used, thereby accommodating a higher image frame rate since less pixel data requires processing. If so desired, other operating parameters, such as scan speed (e.g., linear or rotational movement of the emission 102 and detection 104 systems) or emission patterns 125*a*, 125*b*, can also be controlled or varied in respective manners consistent with the desired field of view or image frame rate or both.

As an exemplary embodiment, a cone beam CT scan of, e.g., a torso area of a subject 110, may be obtained by rotating the emission 102 and detection 104 systems one or more times at a first speed, while obtaining data from, e.g., substantially all of the receptor 132 area at a first frame rate. The emission 102 and detection 104 systems can also be rotated at a different, greater speed, while obtaining data from only a portion of the receptor 132 area (e.g., 8 or 16 rows of the pixel array) at a greater frame rate. The second area may be an area of interest where the greater frame rate is desirable to minimize motion artifacts.

Various other modifications and alternations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus including a flat panel X-ray imaging system adapted to acquire images at a plurality of frame rates and with a plurality of fields of view, comprising:
    an X-ray emission system responsive to at least one emission control signal by providing a plurality of X-ray radiation emissions;
    an X-ray detection system, including a substantially planar X-ray receptor, responsive to at least one detection control signal and respective portions of said plurality of X-ray radiation emissions following exposure thereto of a subject disposed at least partially between said X-ray emission system and said X-ray receptor by providing a plurality of image signals having a plurality of frame rates and corresponding to a plurality of images of said subject, including a combination of one or more of projection, volumetric and cross section views of one or more portions of said subject, with a first portion of said plurality of subject images having a larger field of view (FOV) at a lower one of said plurality of frame rates and a second portion of said plurality of subject images having a smaller FOV at a higher one of said plurality of frame rates; and
    a control system coupled to said X-ray emission and detection systems, and responsive to at least a portion of a plurality of user inputs by providing said at least one emission control signal and said at least one detection control signal.

2. The apparatus of claim 1, wherein said control system provides said at least one emission control signal and said at least one detection control signal such that said X-ray detection system provides a first portion of said plurality of image signals corresponding to said first portion of said plurality of subject images followed by a second portion of said plurality of image signals corresponding to said second portion of said plurality of subject images.

3. The apparatus of claim 1, wherein said plurality of image signals correspond to a plurality of scanning modes including fluoroscopic, radiographic and cone beam computed tomography.

4. The apparatus of claim 1, wherein said one or more projection views comprises fluoroscopic and radiographic images.

5. The apparatus of claim 4, wherein at least one each of said one or more volumetric and cross section views comprises a respective tomographic image.

6. The apparatus of claim 1, wherein at least one each of said one or more volumetric and cross section views comprises a respective tomographic image.

7. The apparatus of claim 1, wherein said control system provides said at least one emission control signal such that said X-ray emission system provides said plurality of X-ray radiation emissions with a plurality of emission patterns.

8. The apparatus of claim 1, wherein said X-ray emission and detection systems rotate at least in part about an axis at a plurality of rotational velocities.

9. The apparatus of claim 1, wherein said X-ray emission and detection systems rotate at least in part about an axis in substantially mutually diametric opposition.

10. The apparatus of claim 1, wherein said X-ray emission and detection systems rotate at least in part about an axis in substantially mutually diametric opposition at a plurality of rotational velocities.

11. The apparatus of claim 1, wherein said first and second portions of said plurality of subject images have first and second mutually dissimilar image resolutions, respectively, associated therewith.

12. The apparatus of claim 11, wherein said first and second mutually dissimilar image resolutions comprise first and second mutually dissimilar temporal resolutions.

13. The apparatus of claim 1, wherein said control system includes a signal processing system responsive to at least another portion of said plurality of user inputs by processing at least a portion of said plurality of image signals to produce a plurality of processed signals corresponding to a composite image in which said first and second portions of said plurality of subject images are combined.

14. The apparatus of claim 1, wherein said control system includes a signal processing system responsive to at least another portion of said plurality of user inputs by processing at least a portion of said plurality of image signals to produce a plurality of processed signals corresponding to a composite image in which respective sub-portions of said first and second portions of said plurality of subject images are combined.

15. The apparatus of claim 1, wherein said control system includes a signal processing system responsive to at least another portion of said plurality of user inputs by processing at least a portion of said plurality of image signals to produce a plurality of processed signals corresponding to a composite image in which said second portion of said plurality of subject images is substituted for a sub-portion of said first portion of said plurality of subject images.

16. An apparatus including a flat panel X-ray imaging system adapted to acquire images at a plurality of frame rates and with a plurality of fields of view, comprising:

X-ray emitter means for responding to at least one emission control signal by providing a plurality of X-ray radiation emissions;

X-ray detector means, including substantially planar X-ray receptor means, for responding to at least one detection control signal and respective portions of said plurality of X-ray ray radiation emissions following exposure thereto of a subject disposed at least partially between said X-ray emission system and said X-ray receptor by providing a plurality of image signals having a plurality of frame rates and corresponding to a plurality of images of said subject, including a combination of one or more of projection, volumetric and cross section views of one or more portions of said subject with a first portion of said plurality of subject images having a larger field of view (FOV) at a lower one of said plurality of frame rates and a second portion of said plurality of subject images having a smaller FOV at a higher one of said plurality of frame rates; and controller means for responding to at least a portion of a plurality of user inputs by providing said at least one emission control signal and said at least one detection control signal.

17. A method for using a flat panel X-ray imaging system to acquire images at a plurality of frame rates and with a plurality of fields of view, comprising:

disposing a subject at least partially between an X-ray radiation source and a substantially planar X-ray receptor; and providing a plurality of X-ray radiation emissions with said X-ray radiation source in response to reception of at least one emission control signal;

providing, with said X-ray receptor, a plurality of image signals in response to reception of at least one detection control signal and respective portions of said plurality of X-ray radiation emissions following exposure thereto of said subject, wherein said plurality of image signals has a plurality of frame rates and corresponds to a plurality of images of said subject including a combination of one or more of projection, volumetric and cross section views of one or more portions of said subject with a first portion of said plurality of subject images having a larger field of view (FOV) at a lower one of said plurality of frame rates and a second portion of said plurality of subject images having a smaller FOV at a higher one of said plurality of frame rates.

* * * * *